United States Patent [19]

Coffey et al.

[11] Patent Number: 5,849,509

[45] Date of Patent: *Dec. 15, 1998

[54] NUCLEAR MATRIX PROTEINS

[75] Inventors: Donald S. Coffey, Lutherville; Alan W. Partin, Baltimore; Robert H. Getzenberg, Branford, all of Md.

[73] Assignee: The Johns Hopkins University School of Medicine, Baltimore, Md.

[*] Notice: The term of this patent shall not extend beyond the expiration date of Pat. No. 5,824,490.

[21] Appl. No.: 488,036

[22] Filed: Jun. 7, 1995

Related U.S. Application Data

[62] Division of Ser. No. 15,624, Feb. 9, 1993, abandoned.

[51] Int. Cl.$^6$ .......................... G01N 33/574; G01N 33/53
[52] U.S. Cl. ........................... 435/7.23; 435/7.1; 436/64; 436/813
[58] Field of Search ..................... 435/7.1, 7.23; 530/387.1, 388.1; 436/64, 813

[56] References Cited

U.S. PATENT DOCUMENTS 4,882,268  11/1989  Penman et al. .

OTHER PUBLICATIONS

Cupo, J.F. (1991) J. Chromatog. 569:389–406.
Getzenberg & Coffey (1990). Molec Endocr. 4:1336–42.
Getzenberg et al. (1991) Biochem. Biophys. Res. Comm. 179:340–44.
Getzenberg et al. (1991) Cancer Res 51:6514–20.
Partin & Coffey (1994) Rec Prog Houm Res. 49:293–331.

Primary Examiner—Toni R. Scheiner
Attorney, Agent, or Firm—Fish & Richardson, P.C.

[57] ABSTRACT

Nuclear matrix proteins (NMP) which are characterized by a defined expression in tissue are provided. These NMPs are useful markers in diagnosing and monitoring the stage of malignancy of a cell. Also provided are substantially purified polypeptides and nucleotide sequences encoding the NMPs of the invention.

4 Claims, 4 Drawing Sheets

NUCLEAR MATRIX PROTEINS

This application is a divisional of the application Ser. No. 08/015,624, filed on Feb. 9, 1993, now abandoned.

This invention was made with Government support under NIH SPORE Grant P50 CA 58236-01 awarded by the National Institutes of Health, DK-19300 National Institute of Arthritis, Diabetes and Digestive and Kidney Diseases and CA 15416, National Cancer Institute.

BACKGROUND OF THE INVENTION

1. Field of the Invention

This invention relates generally to nuclear matrix proteins and specifically to novel nuclear matrix proteins with defined tissue expression patterns in normal cells and cells associated with cell proliferative disorders.

2. Description of Related Art

Advances in recombinant DNA technology have led to the discovery of normal cellular genes (proto-oncogenes and tumor suppressor genes) which control growth, development, and differentiation. Under certain circumstances, regulation-of these genes is altered and normal cells assume neoplastic growth behavior. In some cases, the normal cell phenotype can be restored by various manipulations associated with these genes. There are over 40 known proto-oncogenes and suppressor genes to date, which fall into various categories depending on their functional characteristics. These include, 1) growth factors and growth factor receptors, 2) messengers of intracellular signal transduction pathways, for example, between the cytoplasm and the nucleus, and 3) regulatory proteins influencing gene expression and DNA replication, located both within and outside the nucleus.

During their life span, normal cells begin in an immature state with proliferative potential, pass through sequential stages of differentiation, and eventually end in cell death. Cancer, on the other hand, is a multistep process which can be defined in terms of stages of malignancy wherein the normal orderly progression is aberrant, probably due to alterations in oncogenes, tumor suppressor genes, and other genes. Research an oncogenes and their products has led to a more fundamental understanding of the mechanisms of cancer causation and maintenance allowing more rational means of diagnosing and treating malignancies.

Genes associated with the control of normal growth and differentiation of cells include genes which encode regulatory proteins which influence gene expression and DNA replication. The gene products of many of these genes localize in the nucleus and many are DNA binding proteins. The nucleus of an animal cell contains cellular DNA complexed with protein, referred to as chromatin. The chromatin is organized by the internal skeleton of the nucleus, called the nuclear matrix Nuclear matrix proteins (NMP) associated with DNA may be growth/differentiation regulatory proteins which play a role in the regulation of gene expression in a cell. In cells that have lost their growth regulatory mechanisms, it can be envisioned that a nucleus-specific protein may continuously activate a transcriptional promoter region of a gene, causing over-expression of the gene. Similarly, a nuclear protein which functions as a suppressor to control or suppress the expression of various proto-oncogenes, may be under-expressed or expressed in a mutant form, thereby allowing aberrant expression of a gene which otherwise would be suppressed.

Current cancer tests are generally nonspecific, insensitive and, consequently, of limited clinical application. For example, a biochemical test, widely used for both diagnostic and monitoring of cancer, measures levels of carcinoembryonic antigen (CEA). CEA is an oncofetal antigen detectable in large amounts in embryonal tissue, but in small amounts in normal adult tissues. Serum of patients with certain gastrointestinal cancers contains elevated CEA levels that can be measured by immunological methods. The amount of CEA in serum correlates with the remission or relapse of these tumors, with the levels decreasing abruptly after surgical removal of the tumor. The return of elevated CEA levels signifies a return of malignant cells. CEA, however, is also a normal glycoprotein found at low levels in nearly all adults. Moreover, this protein can be elevated with several nonmalignant conditions and is not elevated in the presence of many cancers. Therefore it is far from ideal as a cancer marker. A similar oncofetal tumor marker is alpha-fetoprotein, an embryonic form of albumin. Again, the antigen is detectable in high amounts in embryonal tissue and in low amounts in normal adults. It is elevated in a number of gastrointestinal malignancies including hepatoma. Like CEA, a decrease correlates with the remission of cancer and a re-elevation with relapse. There is insufficient sensitive and specificity to make this marker useful for screening for malignancy or for monitoring previously diagnosed cancer in any but a few selected cases.

In view of the foregoing, there remains a need for new cancer markers which would allow more effective diagnosis, prognosis and treatment regimes. The identification of NMPs which are associated with the regulation of gene expression or cellular structure in normal and cancer cells would provide ideal markers for identification of the stage of malignancy of a cell.

SUMMARY OF THE INVENTION

The present invention is based in the discovery of novel nuclear matrix proteins (NMP) which have defined patterns of tissue expression in different stages of abnormal growth and malignancy of a cell. The NMPs of the invention are defined by a tissue expression pattern characteristic of any one of the proteins, NPB-1, NPB-2, NPB-3, NPB-4, NPB-5, NPB-6, NPB-7, NP-1, NP-2, NP-3, BPC-1, BPC-2, BPC-3, and PC-1. These proteins were initially identified as being associated with normal prostate tissue (NP), both normal and benign hyperplasia prostate tissue (NBP), benign hyperplasia and cancerous prostate tissue (BPC), or prostate cancer tissue (PC).

The invention provides nucleotides which encode the novel NMPs. The NMPs of the invention provide the basis for a method of detecting a cell proliferative disorder in a subject comprising contacting a cellular component with a reagent which binds to the NMP. The method is especially useful for detecting a cell proliferative disorder in a tissue of the urogenital system, and specifically the prostate.

The invention also provides a method of treating a cell proliferative disorder associated with NPB-1, NPB-2, NPB-3, NPB-4, NPB-5, NPB-6, NPB-7, NP-1, NP-2, NP-3, BPC-1, BPC-2, BPC-3, and PC-1. Such a method may include gene therapy, for example.

DETAILED DESCRIPTION OF THE INVENTION

Figure 1A:
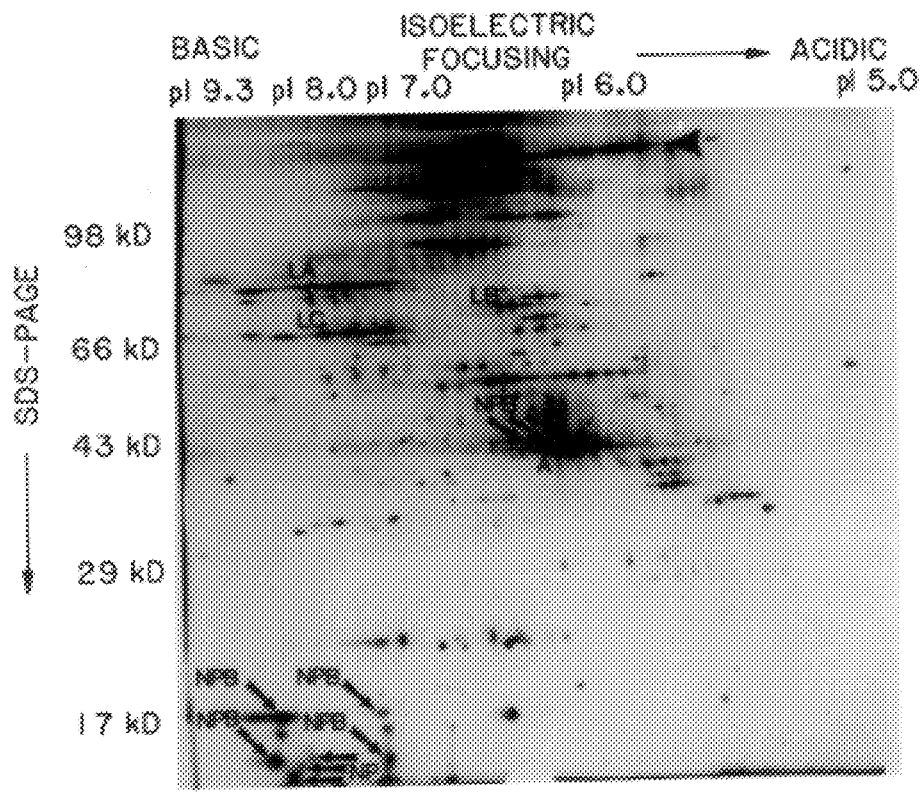
FIG. 1A–C shows nuclear matrix protein composition of normal human prostate (1A), benign prostatic hyperplasia (1B) and prostate cancer (1C). Large arrow panel A. variable group of proteins that were inconsistently present on various types of tissue. Small arrows, proteins that are consistently changed in all tissues and are identified by molecular weight and isoelectric point in table 1. Abbreviations: LA—lamin A, LB—lamin B, LC—lamin C, A—actin, NP—normal prostate, NPB—normal prostate and BPH, BPC—BPH and prostate cancer, PC-prostate cancer, kD—molecular weight in thousands, SDS-PAGE—sodium dodecyl sulfate-polyacrylamide gel electrophoresis and pI—isoelectric point

The present invention provides substantially pure nuclear matrix proteins (NMP) or functional fragments thereof, wherein the protein has a tissue expression pattern characteristic of a protein selected from the group comprising NPB-1, NPB-2, NPB-3, NPB-4, NPB-5, NPB-6, NPB-7, NP-1, NP-2, NP-3, BPC-1, BPC-2, BPC-3, and PC-1. The invention also provides polynucleotide sequences which encode these proteins. The NMPs of the invention can generally be characterized by their presence in a cell during a specific stage of a cell proliferative disorder.

The term "cell-proliferative disorder" denotes malignant as well as non-malignant cell populations which often appear to differ from the surrounding tissue both morphologically and genotypically. Malignancy (i.e, cancer) is a multistep process and the proteins of the invention are associated with three broad steps in the transition from a normal cell to a cancer cell. In broad stages, normal tissue (stage 1) may begin to show signs of hyperplasia (stage 2) or show signs of neoplasia (stage 3). As used herein, "hyperplasia" refers to cells which exhibit abnormal multiplication or abnormal arrangement in a tissue. Included in the term hyperplasia, are benign cellular proliferative disorders, including benign tumors. Proteins of the invention which exhibit a tissue expression pattern in both normal tissue and benign hyperplastic tissue (NPB) (non-malignant) include NPB-1, NPB-2, NPB-3, NPB-4, NPB-5, NPB-6 and NPB-7. The term "tissue expression pattern" refers to the synthesis of a gene product of an NMP gene at a level which is detectable by methods commonly used by those of skill in the art (e.g., SDS-polyacrylamide gel electrophoresis). As used herein, "neoplasia" refers to abnormal new growth, which results in a tumor. Unlike hyperplasia, neoplastic proliferation persists even in the absence of the original stimulus and characterized as uncontrolled and progressive. Malignant neoplasms, or malignant tumors, are distinguished from benign tumors in that the former show a greater degree of anaplasia and have the properties of invasion and metastasis. A protein of the invention, PC-1, is an example of a protein which has an expression pattern seen in malignant neoplasms. The proteins of the invention, BPC-1, BPC-2 and BPC-3 are examples of proteins which are expressed in both benign hyperplastic tissue or tumors and also neoplastic tissues or tumors. On the other hand, proteins NP-1, NP-2 and NP-3 have tissue expression patterns in normal (non-tumor), non-hyperplastic, and non-neoplastic tissue. Thus, the presence of these latter proteins essentially rule out the presence of a cell proliferative disorder.

In summary, BPC-1, BPC-2 and BPC-3 and PC-1 are associated with tumor cells; NPB-1, NPB-2, NPB-3, NPB-4, NPB-5, NPB-6, and NPB-7 are associated with normal and non-malignant hyperplastic or tumor cells; Pc-1 is associated with malignant cells; and NP-1, NP-2, and NP-3 are associated with non-tumor cells. The term "associated with" refers to the correlation between the expression pattern of the protein and the stage of progression to cancer.

The invention provides substantially pure NMPs or functional fragments thereof. As used herein, the term "functional polypeptide" or "functional fragment" refers to a polypeptide which possesses a biological function or activity which is identified through a defined functional assay and which is associated with a particular biologic, morphologic or phenotypic alteration in the cell. The polypeptide fragment possessing biological function can vary from as small as an epitope to which an antibody molecule can bind to as large as a polypeptide capable of participating in the characteristic induction or programming of phenotypic changes within a cell. It is understood that all functional polypeptides encoding all or a functional portion of the NMPs of the invention are also included herein, so long as they are found in the nuclear matrix and exhibit the tissue expression pattern characteristic of a given NMP of the invention. A "functional polynucleotide" denotes a polynucleotide which encodes a functional polypeptide as described herein.

The term "substantially pure" or "isolated" means any NMP functional polypeptide of the present invention, or any gene encoding an NMP functional polypeptide, which is essentially free of other polypeptides or genes, respectively, or of other contaminants with which it might normally be found in nature, and as such exists in a form not found in nature. The invention also provides functional derivatives of the NMPs of the invention. By "functional derivative" is meant the "fragments," "variants," "analogues," or "chemical derivatives" of a molecule. A "fragment" of a molecule, such as any of the DNA or amino acid sequences of the present invention, includes any nucleotide or amino acid subset of the molecule. A "variant" of such molecule refers to a naturally occurring molecule substantially similar to either the entire molecule, or a fragment thereof. An "analog" of a molecule refers to a non-natural molecule substantially similar to either the entire molecule or a fragment thereof.

Procedures which may be used to isolate the NMPs of the invention include those commonly used for the separation of protein substances including, for example; treatment of a sample containing NMP with common precipitants for proteins, followed by fractionation techniques such as ion exchange chromatography, affinity chromatography, molecular sieve chromatography, adsorption chromatography, ultrafiltration and various combinations thereof. The NMPs can be purified from a cell suspension by methods described in U.S. Pat. Nos. 4,885,236 and 4,882,268, for example. Other methods for purification of the polypeptides of the invention will be known to those of skill in the art (see, for example, *Current Protocols In Immunology*, Coligan, et al., eds. 1992, incorporated herein by reference).

The NMP containing fractions can be subjected to SDS PAGE under suitable conditions and the gel slice containing NMP activity or corresponding to the molecular weight of the NMP of interest is recovered. SDS PAGE is performed according to the method of Laemmi, et al., (*Nature,* 227:680, 1970) and is a technique well known to those in the art. Variations in conditions which are within a suitable range are understood to be encompassed within the purification procedure.

The NMP containing fraction from the SDS PAGE is subjected to reverse phase HPLC and eluted with acetonitrile for example. The NMP which is obtained is substantially pure to permit N-terminal amino acid sequencing. The solution is dried under vacuum and redissolved in a small volume of acetonitrile 95% +TFA (0.08%). The concentrated sample is then introduced in a sequencer connected to a phenylthiohydantoine (PTH) analyzer.

The invention provides polynucleotides, such as DNA, cDNA, and RNA, encoding novel NMP functional polypeptides. It is understood that all polynucleotides encoding all or a functional portion of the NMPs of the invention are also included herein, so long as they are found in the nuclear matrix and exhibit the tissue expression pattern characteristic of a given NMP of the invention. Such polynucleotides include both naturally occurring and intentionally manipulated, for example, mutagenized polynucleotides.

The polynucleotide sequence-for NMP also includes antisense sequences and sequences that are degenerate as a result of the genetic code. There are 20 natural amino acids, most of which are specified by more than one codon. Therefore, as long as the amino acid sequence of NMP results in a functional polypeptide (at least, in the case of the sense polynucleotide strand), all degenerate nucleotide sequences are included in the invention. Where the antisense polynucleotide is concerned, the invention embraces all antisense polynucleotides capable of inhibiting production of the NMP polypeptide.

DNA sequences of the invention can be obtained by several methods. For example, the DNA can be isolated using hybridization procedures which are well known in the art. These include, but are not limited to: 1) hybridization of probes to genomic or cDNA libraries to detect shared nucleotide sequences; 2) antibody screening of expression libraries to detect shared structural features; and 3) synthesis by the polymerase chain reaction (PCR). RNA sequences of the invention can be obtained by methods known in the art (See for example, *Current Protocols in Molecular Biology,* Ausubel, et al. eds., 1989, incorporated herein by reference).

The development of specific DNA sequences encoding NMPs of the invention can be obtained by: (1) isolation of a double-stranded DNA sequence from the genomic DNA; (2) chemical manufacture of a DNA sequence to provide the necessary codons for the polypeptide of interest; and (3) in vitro synthesis of a double-stranded DNA sequence by reverse transcription of mRNA isolated from a eukaryotic donor cell. In the latter case, a double-stranded DNA complement of mRNA is eventually formed which is generally referred to as cDNA. Of these three methods for developing specific DNA sequences for use in recombinant procedures, the isolation of genomic DNA isolates is the least common. This is especially true when it is desirable to obtain the microbial expression of mammalian polypeptides due to the presence of introns.

The synthesis of DNA sequences is frequently the method of choice when the entire sequence of amino acid residues of the desired polypeptide product is known. When the entire sequence of amino acid residues of the desired polypeptide is not known, the direct synthesis of DNA sequences is not possible and the method of choice is the formation of cDNA sequences.

Among the standard procedures for isolating cDNA sequences of interest is the formation of plasmid carrying cDNA libraries which are derived from reverse transcription of mRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay, et al., *Nucleic Acid Research,* 11:2325, 1983).

Hybridization procedures are useful for the screening of recombinant clones by using labeled mixed synthetic oligonucleotide probes where each probe is potentially the complete complement of a specific DNA sequence in the hybridization sample which includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. By using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., *Nucleic Acid Research,* 9:879, 1981).

An NMP-containing cDNA library can be screened by injecting the various cDNAs into oocytes, allowing sufficient time for expression of the cDNA gene products to occur, and testing for the presence of the desired cDNA expression product, for example, by using an antibody specific for NMP polypeptide or by using functional assays for NMP activity and a tissue expression pattern characteristic of NMP.

Screening procedures which rely on nucleic acid hybridization make it possible to isolate any gene sequence from any organism, provided the appropriate probe is available. Oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction which utilizes a heterogeneous mixture of denatured double-stranded DNA when the sequence is degenerate. For such screening, hybridization is preferably performed on either single-stranded DNA or denatured double-stranded DNA.

Since the novel DNA sequences of the invention encode essentially all or part of an NMP, it is now a routine matter to prepare, subclone, and express smaller polypeptide fragments of DNA from this or corresponding DNA sequences. Alternatively, by utilizing the DNA fragments disclosed herein which define the unique NMP classes of the invention it is possible, in conjunction with known techniques, to determine the DNA sequences encoding the entire NMP. Such techniques are described in U.S. Pat. No. 4,394,443 and U.S. Pat. No. 4,446,235 which are incorporated herein by reference.

A cDNA expression library, such as lambda gt11, can be screened indirectly for NMP peptides having at least one epitope, using antibodies specific for NMP. Such antibodies can be either polyclonally or monoclonally derived and used to detect expression product indicative of the presence of NMP cDNA.

Polyclonal antibodies are prepared by immunization of an animal, e.g., rabbit, with an immunogenic sample of NMP followed by purification of the antibody by methods well known in the art Antibodies provided in the present invention are immunoreactive with the NMP of the invention. Antibody which consists essentially of pooled monoclonal antibodies with different epitopic specificities, as well as distinct monoclonal antibody preparations are provided. Monoclonal antibodies are made from antigen containing fragments of the protein by methods well known in the art (Kohler, et al., Nature, 256:495, 1975; Current Protocols in Molecular Biology, Ausubel, et al., ed., 1989).

The antibodies of the invention can be used in immunoaffinity chromatography for the isolation of sequences containing an NMP of the present invention. One way by which such immunoaffinity chromatography can be utilized is by the binding of the antibodies of the invention to CNBr-Sepharose-4B or Tresyl activated Sepharose (Pharmacia). These solid phase-bound antibodies can then be used to specifically bind sequences containing NMP from mixtures of other proteins to enable isolation and purification thereof. Bound NMP sequences can be eluted from the affinity chromatographic material using techniques known to those of ordinary skill in the art such as, for example, chaotropic agents, low pH, or urea The production of an NMP DNA sequence can be accomplished by oligonucleotde(s) which are primers for amplification of the genomic polynucleotide encoding an NMP. These unique oligonucleotde primers can be produced based upon identification of the flanking regions contiguous with the polynucleotide encoding the NMP. These oligonucleotide primers comprise sequences which are capable of hybridizing with the flanking nucleotide sequence encoding an NMP polypeptide and sequences complementary thereto.

The primers of the invention include oligonucleotides of sufficient length and appropriate sequence so as to provide specific initiation of polymerization on a significant number of nucleic acids in the polynucleotide encoding the NMP. Specifically, the term "primer" as used herein refers to a sequence comprising two or more deoxyribonucleotides or ribonucleotides, preferably more than three, which sequence is capable of initiating synthesis of a primer extension product, which is substantially complementary to an NMP strand. Experimental conditions conducive to synthesis include the presence of nucleoside triphosphates and an agent for polymerization and extension, such as DNA polymerase and a suitable temperature and pH. The primer is preferably single stranded for maximum efficiency in amplification, but may be double stranded. If double stranded, the primer is first treated to separate the two strands before being used to prepare extension products. Preferably, the primer is an oligodeoxyribonucleotide. The primer must be sufficiently long to prime the synthesis of extension products in the presence of the inducing agent for polymerization and extension of the nucleotides. The exact length of primer will depend on many factors, including temperature, buffer, and nucleotide composition. The oligonucleotide primer typically contains 15–22 or more nucleotides, although it may contain fewer nucleotides.

Primers of the invention are designed to be "substantially" complementary to each strand of polynucleotide encoding the NMP to be amplified. This means that the primers must be sufficiently complementary to hybridize with their respective strands under conditions which allow the agent for polymerization and nucleotide extension to act. In other words, the primers should have sufficient complementarity with the flanking sequences to hybridize therewith and permit amplification of the polynucleotide encoding the receptor NMP. Preferably, the primers have exact complementarity with the flanking sequence strand.

Oligonucleotide primers of the invention are employed in the amplification process which is an enzymatic chain reaction that produces exponential quantities of polynucleotide encoding the NMP relative to the number of reaction steps involved. Typically, one primer is complementary to the negative (−) strand of the polynucleotide encoding the NMP and the other is complementary to the positive (+) strand. Annealing the primers to denatured nucleic acid followed by extension with an enzyme, such as the large fragment of DNA Polymerase I (Klenow) and nucleotides, results in newly synthesized (+) and (−) strands containing the NMP sequence. Because these newly synthesized sequences are also templates, repeated cycles of denaturing, primer annealing, and extension results in exponential production of the sequence (i.e., the NMP polynucleotide sequence) defined by the primer. The product of the chain reaction is a discrete nucleic acid duplex with termini corresponding to the ends of the specific primers employed. Those of skill in the art will know of other amplification methodologies which can also be utilized to increase the copy number of target nucleic acid. These may include, for example, ligation activated transcription (LAT), ligase chain reaction (LCR), and strand displacement activation (SDA), although PCR is the preferred method.

The oligonucleotide primers of the invention may be prepared using any suitable method, such as conventional phosphotriester and phosphodiester methods or automated embodiments thereof. In one such automated embodiment, diethylphosphoramidites are used as starting materials and may be synthesized as described by Beaucage, et al. (Tetrahedron Letters, 2:1859–1862, 1981). One method for synthesizing oligonucleotides on a modified solid support is described in U.S. Pat. No. 4,458,066. One method of amplification which can be used according to this invention is the polymerase chain reaction (PCR) described in U.S. Pat. Nos. 4,683,202 and 4,683,195.

Any nucleic acid specimen, in purified or nonpurified form, can be utilized as the starting nucleic acid for the above procedures, provided it contains, or is suspected of containing, the specific nucleic acid sequence of an NMP of the invention. Thus, the process may employ, for example, DNA or RNA (including mRNA), wherein DNA or RNA may be single stranded or double stranded. In the event that RNA is to be used as a template, enzymes, and/or conditions optimal for reverse transcribing the template to DNA would be utilized. In addition, a DNA-RNA hybrid which contains one strand of each may be utilized. A mixture of nucleic acids may also be employed, or the nucleic acids produced in a previous amplification reaction herein, using the same or different primers may be so utilized. The specific nucleic acid sequence to be amplified, (i.e., NMP sequence), may be a fraction of a larger molecule or can be present initially as a discrete molecule, so that the specific sequence constitutes the entire nucleic acid. It is not necessary that the sequence to be amplified be present initially in a pure form; it may be a minor fraction of a complex mixture, such as contained in whole human DNA.

DNA or RNA utilized herein may be extracted from a body sample, such as prostate tissue, or various other tissue, by a variety of techniques such as that described by Maniatis, et al. (*Molecular Cloning,* 280:281, 1982). If the extracted sample is impure (such as plasma, serum, ejaculate or blood), it may be treated before amplification with an amount of a reagent effective to open the cells, fluids, tissues, or animal cell membranes of the sample, and to expose and/or separate the strand(s) of the nucleic acid(s). This lysing and nucleic acid denaturing step to expose and separate the strands will allow amplification to occur much more readily.

Where the target nucleic acid sequence of the sample contains two strands, it is necessary to separate the strands of the nucleic acid before it can be used as the template. Strand separation can be effected either as a separate step or simultaneously with the synthesis of the primer extension products. This strand separation can be accomplished using various suitable denaturing conditions, including physical, chemical, or enzymatic means, the word "denaturing" includes all such means. One physical method of separating nucleic acid strands involves heating the nucleic acid until it is denatured. Typical heat denaturation may involve temperatures ranging from about 80° to 105° C. for times ranging from about 1 to 10 minutes. Strand separation may also be induced by an enzyme from the class of enzymes known as helicases or by the enzyme RecA, which has helicase activity, and in the presence of riboATP, is known to denature DNA. The reaction conditions suitable for stand separation of nucleic acids with helicases are described by Kuhn Hoffmann-Berling (*CSH-Quantitative Biology,* 43:63, 1978) and techniques for using RecA are reviewed in C. Radding (*Ann. Rev. Genetics,* 16:405–437, 1982).

If the nucleic acid containing the sequence to be amplified is single stranded, its complement is synthesized by adding one or two oligonucleotide primers. If a single primer is utilized, a primer extension product is synthesized in the presence of primer, an agent for polymerization, and the four nucleoside triphosphates described below. The product will be partially complementary to the single-stranded nucleic acid and will hybridize with a single-stranded nucleic acid to form a duplex of unequal length strands that may then be separated into single strands to produce two single separated complementary strands. Alternatively, two primers may be added to the single-stranded nucleic acid and the reaction carried out as described.

When complementary strands of nucleic acid or acids are separated, regardless of whether the nucleic acid was originally double or single stranded, the separated strands are ready to be used as a template for the synthesis of additional nucleic acid strands. This synthesis is performed under conditions allowing hybridization of primers to templates to occur. Generally synthesis occurs in a buffered aqueous solution, preferably at a pH of 7–9, most preferably about 8. Preferably, a molar excess (for genomic nucleic acid, usually about $10^8$:1 primer:template) of the two oligonucleotide primers is added to the buffer containing the separated template strands. It is understood, however, that the amount of complementary strand may not be known if the process of the invention is used for diagnostic applications, so that the amount of primer relative to the amount of complementary strand cannot be determined with certainty. As a practical matter, however, the amount of primer added will generally be in molar excess over the amount of complementary strand (template) when the sequence to be amplified is contained in a mixture of complicated long-chain nucleic acid strands. A large molar excess is preferred to improve the efficiency of the process.

The deoxyribonucleotide triphosphates dATP, dCTP, dGTP, and dTTP are added to the synthesis mixture, either separately or together with the primers, in adequate amounts and the resulting solution is heated to about 90°–100° C. from about 1 to 10 minutes, preferably from 1 to 4 minutes. After this heating period, the solution is allowed to cool to room temperature, which is preferable for the primer hybridization. To the cooled mixture is added an appropriate agent for effecting the primer extension reaction (called herein "agent for polymerization"), and the reaction is allowed to occur under conditions known in the art. The agent for polymerization may also be added together with the other reagents if it is heat stable. This synthesis (or amplification) reaction may occur at room temperature up to a temperature above which the agent for polymerization no longer functions. Thus, for example, if DNA polymerase is used as the agent, the temperature is generally no greater than about 40° C. Most conveniently the reaction occurs at room temperature.

The agent for polymerization may be any compound or system which will function to accomplish the synthesis of primer extension products, including enzymes. Suitable enzymes for this purpose include, for example, *E. coil* DNA polymerase I, Klenow fragment of *E. coli* DNA polymerase I, T4 DNA polymerase, other available DNA polymerases, polymerase muteins, reverse transcriptase, and other enzymes, including heat-stable enzymes (i.e., those enzymes which perform primer extension after being subjected to temperatures sufficiently elevated to cause denaturation). Suitable enzymes will facilitate combination of the nucleotides in the proper manner to form the primer extension products which are complementary to each NMP nucleic acid strand. Generally, the synthesis will be initiated at the 3' end of each primer and proceed in the 5' direction along the template strand, until synthesis terminates, producing molecules of different lengths. There may be agents for polymerization, however, which initiate synthesis at the 5' end and proceed in the other direction, using the same process as described above.

The newly synthesized NMP strand and its complementary nucleic acid strand will form a double-stranded molecule under hybridizing conditions described above and this hybrid is used in subsequent steps of the process. In the next step, the newly synthesized double-stranded molecule is subjected to denaturing conditions using any of the procedures described above to provide single-stranded molecules.

The above process is repeated on the single-stranded molecules. Additional agent for polymerization, nucleotides, and primers may be added, if necessary, for the reaction to proceed under the conditions prescribed above. Again, the synthesis will be initiated at one end of each of the oligonucleotide primers and will proceed along the single strands of the template to produce additional nucleic acid. After this step, half of the extension product will consist of the specific nucleic acid sequence bounded by the two primers.

The steps of denaturing and extension product synthesis can be repeated as often as needed to amplify the NMP nucleic acid sequence to the extent necessary for detection. The amount of the specific nucleic acid sequence produced will accumulate in an exponential fashion.

Sequences amplified by the methods of the invention can be further evaluated, detected, cloned, sequenced, and the like, either in solution or after binding to a solid support, by any method usually applied to the detection of a specific DNA sequence such as PCR, oligomer restriction (Saiki, et al., *Bio/Technology,* 3:1008–1012, 1985), allele-specific oligonucleotide (ASO) probe analysis (Conner, et al., *Proc. Nail. Acad. Sci. USA,* 80:278, 1983), oligonucleotde ligation assays (OLAs) (Landegren, et al., *Science,* 241:1077, 1988), and the like. Molecular techniques for DNA analysis have been reviewed (Landegren, et al., *Science,* 242:229–237, 1988).

DNA sequences encoding NMP can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, in other words when the foreign DNA is continuously maintained in the host, are known in the art.

In the present invention, the NMP polynucleotide sequences may be inserted into a recombinant expression vector. The term "recombinant expression vector" refers to a plasmid, virus or other vehicle known in the art that has been manipulated by insertion or incorporation of the NMP nucleic acid sequences. Such expression vectors contain a promoter sequence which facilitates the efficient transcription of the inserted nucleic acid sequence of the host. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg et al., *Gene* 56:125, 1987), the pMSXND expression vector for expression in mammalian cells (Lee and Nathans, *J. Biol. Chem.* 263:3521, 1988) and baculovirus-derived vectors for expression in insect cells. The DNA segment can be present in the vector operably linked to regulatory elements, for example, a promoter (e.g., T7, metallothionein 1, or polyhedrin promoters).

Polynucleotide sequences encoding NMP can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art. Such vectors are used to incorporate DNA sequences of the invention.

Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method by procedures well known in the art. Alternatively, $MgCl_6$ or RbCl can be used. Transformation can also be performed after forming a protoplast of the host cell or by electroporation.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with DNA sequences encoding the NMP of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (*Eukaryotic Viral Vectors*, Cold Spring Harbor Laboratory, Gluzman ed., 1982).

Isolation and purification of microbially expressed protein, or fragments thereof provided by the invention, may be carried out by conventional means including preparative chromatography and immunological separations involving monoclonal or polyclonal antibodies. Antibodies provided in the present invention are immunoreactive with NMP polypeptide or fragments thereof.

The NMP polypeptide of the invention includes fragments and conservative variations of the polypeptides. Minor modifications of the NMP primary amino acid sequence may result in proteins which have substantially equivalent activity as compared to the NMP polypeptide described herein. Such modifications may be deliberate, as by site-directed mutagenesis, or may be spontaneous. All of the polypeptides produced by these modifications are included herein as long as the biological activity of NMP still exists. Further, deletion of one or more amino acids can also result in a modification of the structure of the resultant molecule without significantly altering its biological activity. This can lead to the-development of a smaller active molecule which would have broader utility.

The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like.

Peptides of the invention can be synthesized by the well known solid phase peptide synthesis methods described Merrifield, *J. Am. Chem. Sac.,* 85:2149, 1962), and Stewart and Young, *Solid Phase Peptides Synthesis*, (Freeman, San Francisco, 1969, pp27–62), using a copoly(styrene-divinylbenzene) containing 0.1–1.0 mMol amines/g polymer. On completion of chemical synthesis, the peptides can be deprotected and cleaved from the polymer by treatment with liquid HF-10% anisole for about ¼–1 hours at 0° C. After evaporation of the reagents, the peptides are extracted from the polymer with 1% acetic acid solution which is then lyophilized to yield the crude material. This can normally be purified by such techniques as gel filtration on Sephadex G-15 using 5% acetic acid as a solvent. Lyophilization of appropriate fractions of the column will yield the homogeneous peptide or peptide derivatives, which can then be characterized by such standard techniques as amino acid analysis, thin layer chromatography, high performance liquid chromatography, ultraviolet absorption spectroscopy, molar rotation, solubility, and quantitated by the solid phase Edman degradation.

The invention includes polyclonal and monoclonal antibodies immunoreactive with NMP polypeptide or immunogenic fragments thereof. If desired, polygonal antibodies can be further purified, for example, by binding to and elution from a matrix to which NMP polypeptide is bound. Those of skill in the art will know of various other techniques common in the immunology arts for purification and/or concentration of polyclonal antibodies, as well as monoclonal antibodies. Antibody which consists essentially of pooled monoclonal antibodies with different epitopic specificities, as well as distinct monoclonal antibody preparations are provided. The term antibody or, immunoglobulin as used in this invention includes intact molecules as well as fragments thereof, such as Fab and $F(ab')_2$, which are functionally capable of binding an epitopic determinant on NMP.

A preferred method for the identification and isolation of antibody binding domain which exhibit binding with NMP is the bacteriophage λ vector system. This vector system has been used to express a combinatorial library of Fab fragments from the mouse antibody repertoire in *Escherichia coli* (Huse, et al., *Science,* 246:1275–1281, 1989) and from the human antibody repertoire (Mullinax, et al., *Proc. Natl. Acad. Sci.,* 87:8095–8099, 1990). As described therein, receptors (Fab molecules) exhibiting binding for a preselected ligand were identified and isolated from these antibody expression libraries. This methodology can also be applied to hybridoma cell lines expressing monoclonal antibodies with binding for a preselected ligand. Hybridomas which secrete a desired monoclonal antibody can be produced in various ways using techniques well understood by those having ordinary skill in the art and will not be repeated here. Details of these techniques are described in such references as *Monoclonal Antibodies-Hybridomas: A New Dimension in Biological Analysis,* Edited by Roger H. Kennett et al., Plenum Press, 1980; and U.S. Pat. No. 4,172,124, incorporated herein by reference.

As used herein, the term "cell-proliferative disorder" denotes malignant as well as non-malignant (or benign) disorders. This term further encompasses hyperplastic disorders. The cells comprising these proliferative disorders often appear morphologically and genotypically to differ from the surrounding normal tissue. As noted above, cell-proliferative disorders may be associated, for example, with expression or absence of expression of the NMPs of the invention. Expression of NMP at an inappropriate time during the cell cycle or in an incorrect cell type may result in a cell-proliferative disorder. The NMP polynucleotide in the form of an antisense polynucleotide is useful in treating hyperplasia and malignancies of the various organ systems, particularly, for example, those of urogenital origin such as the prostate. In addition, hyperplasia and malignancies of such organs as the kidney and bladder can be treated using the NMP polynucleotides of the invention. Essentially, any disorder which is etiologically linked to expression of NMP could be considered susceptible to treatment with a reagent of the invention which modulates NMP expression. The term "modulate" envisions the suppression of expression of NMP when it is inappropriately expressed or augmentation of NMP expression when it is under-expressed or when the NMP expressed is a mutant form of the polypeptide. When a cell-proliferative disorder is associated with NMP expression, (e.g., BPC-1, 2, 3 and PC-1), such suppressive reagents as antisense NMP polynucleotide sequence or NMP binding antibody can be introduced to a cell. Alternatively, when a cell proliferative disorder is associated with under-expression or expression of a mutant NMP polypeptide (e.g., NPB 1–7 and NP-1–3), a sense polynucleotide sequence (the DNA coding strand) or NMP polypeptide can be introduced into the cell.

The invention provides a method for detecting a cell expressing NMP or a cell proliferative disorder associated with NMP in a subject comprising contacting a cell component suspected of expressing NMP or having a NMP associated disorder, with a reagent which binds to the component. The cell component can be nucleic acid, such as DNA or RNA, or protein. When the component is nucleic acid, the reagent is a nucleic acid probe or PCR primer. When the cell component is protein, the reagent is an antibody probe. The probes are directly or indirectly detectably labeled, for example, with a radioisotope, a fluorescent compound, a bioluminescent compound, a chemiluminescent compound, a metal chelator, or an enzyme. Those of ordinary skill in the art will know of other suitable labels for binding to the probe or will be able to ascertain such, using routine experimentation.

For purposes of the invention, an antibody or nucleic acid probe specific for NMP may be used to detect the presence of NMP polypeptide (using antibody) or polynucleotide (using nucleic acid probe) in biological fluids or tissues. Oligonucleotide primers based on any coding sequence region in the NMP sequence are useful for amplifying DNA, for example by PCR. Any specimen containing a detectable amount of antigen can be used. A preferred sample of this invention, especially for detecting prostate cancer, is tissue of urogenital origin, specifically tissue of the prostate. Alternatively, biological fluids which may contain cells indicative of an NMP-associated cell-proliferative disorder, such as ejaculate or urine, may be used. Preferably the subject is human.

Another technique which may also result in greater sensitivity consists of coupling the probe to low molecular weight haptens. These haptens can then be specifically detected by means of a second reaction. For example, it is common to use such haptens as biotin, which reacts with avidin, or dinitrophenol, pyridoxal, and fluorescein, which can react with specific antihapten antibodies.

The method for detecting a cell expressing a particular NMP of the invention or a cell-proliferative disorder associated with an NMP, described above, can be utilized for detection of residual prostate cancer or other malignancies or benign hyperplasia conditions in a subject in a state of clinical remission. Additionally, the method for detecting NMP polypeptide in cells is useful for detecting a cell-proliferative disorder by identifying cells expressing specific NMPs in comparison with NMPs expressed in normal cells. Using the method of the invention, NMP expression can be identified in a cell and the appropriate course of treatment can be employed (e.g., sense or antisense gene therapy, as well as conventional chemotherapy). Since the expression pattern of the NMPs of the invention vary with the stage of malignancy of a cell, a sample such as prostate issue can be screened with a panel of NMP-specific reagents (e.g., nucleic acid probes or antibodies to NMPs) to detect NMP expression and diagnose the stage of malignancy of the cell.

The monoclonal antibodies of the invention are suited for use, for example, in immunoassays in which they can be utilized in liquid phase or bound to a solid phase carrier. In addition, the monoclonal antibodies in these immunoassays can be detectably labeled in various ways. Examples of types of immunoassays which can utilize monoclonal antibodies of the invention are competitive and noncompetitive immunoassays in either a direct or indirect format. Examples of such immunoassays are the radioimmunoassay (RIA) and the sandwich (immunometric) assay. Detection of the antigens using the monoclonal antibodies of the invention can be done utilizing immunoassays which are run in either the forward, reverse, or simultaneous modes, including immunohistochemical assays on physiological samples. Alternatively, antibody of the invention can be used to detect NMPs present in electrophoretically dispersed gel protocols such as Western blots and 2-dimensional gels. Those of skill in the art will know, or can readily discern, other immunoassay formats without undue experimentation.

The monoclonal antibodies of the invention can be bound to many different carriers and used to detect the presence of NMP. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibodies, or will be able to ascertain such using routine experimentation.

In performing the assays it may be desirable to include certain "blockers" in the incubation medium (usually added with the labeled soluble antibody). The "blockers" are added to assure that non-specific proteins, proteases, or anti-heterophilic immunoglobulins to anti-NMP immunoglobulins present in the experimental sample do not cross-ink or destroy the antibodies on the solid phase support, or the radiolabeled indicator antibody, to yield false positive or false negative results. The selection of "blockers" therefore may add substantially to the specificity of the assays described in the present invention.

It has been found that a number of nonrelevant (i.e., nonspecific) antibodies of the same class or subclass (isotype) as those used in the assays (e.g., IgG1, IgG2a, IgM, etc.) can be used as "blockers". The concentration of the "blockers" (normally 1–100 µg/µl) is important, in order to maintain the proper sensitivity yet inhibit any unwanted interference by mutually occurring cross reactive proteins in the specimen.

As used in this invention, the term "epitope" includes any determinant capable of specific interaction with the monoclonal antibodies of the invention. Epitopic determinants usually consist of chemically active surface groupings of molecules such as amino acids or sugar side chains and usually have specific three dimensional structural characteristics, as well as specific charge characteristics.

In using the monoclonal antibodies of the invention for the in vivo detection of antigen, the detectably labeled monoclonal antibody is given in a dose which is diagnostically effective. The term "diagnostically effective" means that the amount of detectably labeled monoclonal antibody is administered in sufficient quantity to enable detection of the site having the NMP antigen for which the monoclonal antibody is specific.

The concentration of detectably labeled monoclonal antibody which is administered should be sufficient such that the binding to those cells having NMP is detectable compared to the background. Further, it is desirable that the detectably labeled monoclonal antibody be rapidly cleared from the circulatory system in order to give the best target-to-background signal ratio.

As a rule, the dosage of detectably labeled monoclonal antibody for in vivo diagnosis will vary depending on such factors as age, sex, and extent of disease of the individual. The dosage of monoclonal antibody can vary from about 0.001 mg/m$^2$ to about 500 mg/m$^2$, preferably 0.1 mg/m$^2$ to about 200 mg/m$^2$, most preferably about 0.1 mg/m$^2$ to about 10 mg/m$^2$. Such dosages may vary, for example, depending on whether multiple injections are given, tumor burden, and other factors known to those of skill in the art.

For in vivo diagnostic imaging, the type of detection instrument available is a major factor in selecting a given radioisotope. The radioisotope chosen must have a type of decay which is detectable for a given type of instrument. Still another important factor in selecting a radioisotope for in vivo diagnosis is that the half-life of the radioisotope be long enough so that it is still detectable at the time of maximum uptake by the target, but short enough so that deleterious radiation with respect to the host is minimized. Ideally, a radioisotope used for in vivo imaging will lack a particle emission, but produce a large number of photons in the 140–250 keV range, which may be readily detected by conventional gamma cameras.

For in vivo diagnosis, radioisotopes may be bound to immunoglobulin either directly or indirectly by using an intermediate functional group. Intermediate functional groups which often are used to bind radioisotopes which exist as metallic ions to immunoglobulins are the bifunctional chelating agents such as diethylenetriaminepentacetic acid (DTPA) and ethylenediaminetetraacetic acid (EDTA) and similar molecules. Typical examples of metallic ions which can be bound to the monoclonal antibodies of the invention are $^{111}$In, $^{97}$Ru, $^{67}$Ga, $^{68}$Ga, $^{72}$As, $^{89}$Zr, and $^{201}$Tl.

The monoclonal antibodies of the invention can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements which are particularly useful in such techniques include $^{157}$Gd, $^{55}$Mn, $^{162}$Dy, $^{52}$Cr, and $^{56}$Fe.

The monoclonal antibodies of the invention can be used to monitor the course of amelioration of NMP associated cell-proliferative disorder. Thus, by measuring the increase or decrease in the number of calls expressing a NMP or changes in NMP present in various body fluids, such as ejaculate or urine, it would be possible to determine whether a particular therapeutic regiment aimed at ameliorating the disorder is effective.

The monoclonal antibodies of the invention can also be used, alone or in combination with effector cells (Douillard, et al. *Hybridoma,* 5 Supp.1:S139, 1986), for immunotherapy in an animal having a cell proliferative disorder which expresses NMP polypeptide with epitopes reactive with the monoclonal antibodies of the invention.

When used for immunotherapy, the monoclonal antibodies of the invention may be unlabeled or labeled wfi a therapeutic agent. These agents can be coupled either directly or indirectly to the monoclonal antibodies of the invention. One example of indirect coupling is by use of a spacer moiety. These spacer moieties, in turn, can be either insoluble or soluble (Diener, et al., *Science,* 231:148, 1986) and can be selected to enable drug release from the monoclonal antibody molecule at the target site. Examples of therapeutic agents which can be coupled to the monoclonal antibodies of the invention for immunotherapy are drugs, radioisotopes, lectins, and toxins.

The drugs which can be conjugated to the monoclonal antibodies of the invention include non-proteinaceous as well as proteinaceous drugs. The terms "non-proteinaceous drugs" encompasses compounds which are classically referred to as drugs, for example, mitomycin C, daunorubicin, and vinblastine.

The proteinaceous drugs with which the monoclonal antibodies of the invention can be labeled include immunomodulators and other biological response modifiers. The term "biological response modifiers" encompasses substances which are involved in modifying the immune response in such manner as to enhance the destruction of an NMP-associated tumor for which the monoclonal antibodies of the invention are specific. Examples of immune response modifiers include such compounds as lymphokines. Lymphokines include tumor necrosis factor, the interleukins, lymphotoxin, macrophage activating factor, migration inhibition factor, colony stimulating factor, and interferon. Interferons with which the monoclonal antibodies of the invention can be labeled include alpha-interferon, beta-interferon and gamma-interferon and their subtypes.

In using radioisotopically conjugated monoclonal antibodies of the invention for immunotherapy certain isotypes may be more preferable than others depending on such factors as tumor cell distribution as well as isotope stability and emission. If desired, the tumor cell distribution can be evaluated by the in vivo diagnostic techniques described above. Depending on the cell proliferative disease some emitters may be preferable to others. In general, alpha and beta particle-emitting radioisotopes are preferred in immunotherapy.

For example, if an animal has solid tumor foci a high energy beta emitter capable of penetrating several millimeters of tissue, such as $^{90}$Y, may be preferable. On the other hand, if the cell proliferative disorder consists of simple target cells, as in the case of leukemia, a short range, high energy alpha emitter, such as $^{212}$Bi, may be preferable. Examples of radioisotopes which can be bound to the monoclonal antibodies of the invention for therapeutic purposes are $^{125}$I, $^{131}$I, $^{90}$Y, $^{67}$Cu, $^{212}$Bi, $^{211}$At, $^{212}$Pb, $^{47}$Sc, $^{109}$Pd, $^{65}$Zn, and $^{188}$Re.

Lectins are proteins, usually isolated from plant material, which bind to specific sugar moieties. Many lectins are also able to agglutinate cells and stimulate lymphocytes. However, ricin is a toxic lectin which has been used immunotherapeutically. This is preferably accomplished by binding the alpha-peptide chain of ricin, which is responsible for toxicity, to the antibody molecule to enable site specific delivery of the toxic effect.

Toxins are poisonous substances produced by plants, animals, or microorganisms, that, in sufficient dose, are often lethal. Diphtheria toxin is a substance produced by *Corynebacterium diphtheria* which can be used therapeutically. This toxin consists of an alpha and beta subunit which under proper conditions can be separated. The toxic A component can be bound to an antibody and used for site specific delivery to a NMP bearing cell. Other therapeutic agents which can be coupled to the monoclonal antibodies of the invention are known, or can be easily ascertained, by those of ordinary skill in the art.

The labeled or unlabeled monoclonal antibodies of the invention can also be used in combination with therapeutic agents such as those described above. Especially preferred are therapeutic combinations comprising the monoclonal antibody of the invention and immunomodulators and other biological response modifiers.

Thus, for example, the monoclonal antibodies of the invention can be used in combination with alpha-interferon. This treatment modality enhances monoclonal antibody targeting of carcinomas by increasing the expression of monoclonal antibody reactive antigen by the carcinoma cells (Greiner, et al., *Science, 235:895, 1987*). Alternatively, the monoclonal antibody of the invention could be used, for example, in combination with gamma-interferon to thereby activate and increase the expression of Fc receptors by effector cells which, in turn, results in an enhanced binding-of the monoclonal antibody to the effector cell and killing of target tumor cells. Those of skill in the art will be able to select from the various biological response modifiers to create a desired effector function which enhances the efficacy of the monoclonal antibody of the invention.

When the monoclonal antibody of the invention is used in combination with various therapeutic agents, such as those described herein, the administration of the monoclonal antibody and the therapeutic agent usually occurs substantially contemporaneously. The term "substantially contemporaneously" means that the monoclonal antibody and the therapeutic agent are administered reasonably close together with respect to time. Usually, it is preferred to administer the therapeutic agent before the monoclonal antibody. For example, the therapeutic agent can be administered 1 to 6 days before the monoclonal antibody. The administration of the therapeutic agent can be daily, or at any other interval, depending upon such factors, for example, as the nature of the tumor, the condition of the patient and half-life of the agent.

Using monoclonal antibodies of the invention, it is possible to design therapies combining all of the characteristics described herein. For example, in a given situation it may be desirable to administer a therapeutic agent, or agents, prior to the administration of the monoclonal antibodies of the invention in combination with effector cells and the same, or different, therapeutic agent or agents. For example, it may be desirable to treat patients with prostate, kidney or bladder carcinoma by first administering gamma-interferon and interleukin-2 daily for 3 to 5 days, and on day 5 administer the monoclonal antibody of the invention in combination with effector cells as well as gamma–interferon, and interleukin-2.

It is also possible to utilize liposomes with the monoclonal antibodies of the invention in their membrane to specifically deliver the liposome to the tumor expressing NMP. These liposomes can be produced such that they contain, in addition to the monoclonal antibody, such immunotherapeutic agents as those described above which would then be released at the tumor site (Wolff, et al., *Biochemical et Biophysical Acta,* 802:259, 1984).

The dosage ranges for the administration of monoclonal antibodies of the invention are those large enough to produce the desired effect in which the symptoms of the malignant disease are ameliorated. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any complication. Dosage can vary from about 0.1 mg/kg to about 2000 mg/kg, preferably about 0.1 mg/kg to about 500 mg/kg, in one or more dose administrations daily, for one or several days. Generally, when the monoclonal antibodies of the invention are administered conjugated with therapeutic agents, lower dosages, comparable to those used for in vivo diagnostic imaging, can be used.

The monoclonal antibodies of the invention can be administered parenterally by injection or by gradual perfusion over time. The monoclonal antibodies of the invention can be administered intravenously, intraperitoneally, intramuscularly, subcutaneously, intracavity, or transdermally, alone or in combination with effector cells.

The present invention also provides a method for treating a subject with an NMP-associated cell-proliferative disorder using an NMP nucleotide sequence. An NMP nucleotide sequence which may encode a suppressor polypeptide may be under-expressed as compared to expression in a normal cell, therefore it is possible to design appropriate therapeutic or diagnostic techniques directed to this sequence. Thus, where a cell-proliferative disorder is associated with the expression of an NMP associated with malignancy, nucleic acid sequences that interfere with NMP expression at the translational level can be used. This approach utilizes, for example, antisense nucleic acid and ribozymes to block translation of a specific NMP mRNA, either by masking that mRNA with an antisense nucleic acid or by cleaving it with a ribozyme. In cases when a cell proliferative disorder or abnormal cell phenotype is associated with the under expression of NMP suppressor for example, nucleic acid sequences encoding NMP (sense) could be administered to the subject with the disorder.

Antisense nucleic acids are DNA or RNA molecules that are complementary to at least a portion of a specific mRNA molecule (Weintraub, *Scientific American*, 262:40, 1990). In the cell, the antisense nucleic acids hybridize to the corresponding mRNA, forming a double-stranded molecule. The antisense nucleic acids interfere with the translation of the mRNA since the cell will not translate a mRNA that is double-stranded. Antisense oligomers of about 15 nucleotides are preferred, since they are easily synthesized and are less likely to cause problems than larger molecules when introduced into the target NMP-producing cell. The use of antisense methods to inhibit the in vitro translation of genes is well known in the art (Marcus-Sakura, *Anal.Biochem.*, 172:289, 1988).

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, *J.Amer.Med Assn.*, 260:3030, 1988). A major advantage of this approach is that, because they are sequence-specific, only mRNAs with particular sequences are inactivated.

There are two basic types of ribozymes namely, tetrahymena-type (Hasselhoff, *Nature*, 334:585, 1988) and "hammerhead"-type. Tetrahymena-type ribozymes recognize sequences which are four bases in length, while "hammerhead"-type is ribozymes recognize base sequences 11–18 bases in length. The longer the recognition sequence, the greater the likelihood that that sequence will occur exclusively in the target mRNA species. Consequently, hammerhead-type ribozymes are preferable to tetrahymena-type ribozymes for inactivating a specific mRNA species and 18-based recognition sequences are preferable to shorter recognition sequences.

The present invention also provides gene therapy for the treatment of cell proliferative disorders which are mediated by NMP. Such therapy would achieve its therapeutic effect by introduction of the appropriate NMP polynucleotide (antisense or sense), into cells of subjects having the proliferative disorder. Delivery of antisense NMP polynucleotide can be achieved using a recombinant expression vector such as a chimeric virus or a colloidal dispersion system. Disorders associated with under-expression of an NMP or expression of a cancer-associated NMP, could be treated using gene therapy with sense or antisense nucleotide sequences, respectively.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. By inserting a NMP sequence of interest into the viral vector, along with another gene which encodes the ligand for a receptor on a specific target cell, for example, the vector is now target specific. Retroviral vectors can be made target specific by inserting, for example, a polynucleotide encoding a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome to allow target specific delivery of the retroviral vector containing the NMP sense or antisense polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal include but are not limited to $\psi$2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Alternatively, NIH 3T3 or other tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for NMP antisense polynucleotides a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2–4.0 urn can encapsulate a substantial percentage of an aqueous buffer containing large macromolecules. RNA, DNA and intact virions can be encapsulated within the aqueous interior and be delivered to cells in a biologically active form (Fraley, et al., *Trends Biochem. Sci.*, 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., *Biotechniques*, 6:682, 1988).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14–18 carbon atoms, particularly from 16–18 carbon atoms, and is saturated. Illustrative phospholipids include egg phosphatidylcholine, dipalmitoylphosphatidylcholine and distearoylphosphatidylcholine.

The targeting of liposomes has been classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

In general, the compounds bound to the surface of the targeted delivery system will be ligands and receptors which will allow the targeted delivery system to find and "home in" on the desired cells. A ligand may be any compound of interest which will bind to another compound, such as a receptor.

In general, surface membrane proteins which bind to specific effector molecules are referred to as receptors. In the present invention, antibodies of the invention are preferred receptors. Antibodies can be used to target liposomes to specific cell-surface ligands, in this case the NMPs of choice. Preferably, the target tissue is urogenital and specifically is prostate tissue. Kidney and bladder tissue may also be utilized. A number of procedures can be used to covalently attach either polyclonal or monoclonal antibodies to a liposome bilayer. Antibody-targeted liposomes can include monoclonal or polyclonal antibodies or fragments thereof such as Fab, or F(ab')$_2$, as long as they bind efficiently to an the antgenic epitope on the target cells.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents and inert gases and the like.

The invention also relates to a method for preparing a medicament or pharmaceutical composition comprising the polynucleotides or the monoclonal antibodies of the invention, the medicament being used for therapy of NMP associated cell proliferative disorders.

The NMPs of the invention are useful as a screening tool for compositions which affect an NMP of a cell. Thus, in another embodiment, the invention provides a method for identifying a composition which affects an NMP comprising incubating the components, which include the composition to be tested and the cell (or cell suspension), under conditions sufficient to allow the components to interact, then subsequently measuring the effect of the composition on the NMP. The observed effect on the NMP may be either inhibitory or stimulatory.

For example, in a malignant cell of the prostate, compositions which are inhibitory to BPC-1, BPC-2, BPC-3, or PC-1 expression can be identified by measuring the level of the NMP in the cell or cell extract before and after treatment with the composition. Alternatively, the levels of NP-1, NP-2, or NP-3 can be monitored to identify compositions which stimulate expression of these NMPs, found in normal cells.

The material for use in the assay of the invention are ideally suited for the preparation of a kit. Such a kit may comprise a carrier means being compartmentalized to receive in close confinement one or more container means such as vials, tubes, and the like, each of the container means comprising one of the separate elements to be used in the method.

For example, one of the container means may comprise a probe which is or can be detectably labelled. Such probe may be an antibody or nucleotide specific for a target protein or a target nucleic acid, respectively, wherein the target is indicative, or correlates with, the presence of an NMP of the invention. Where the kit utilizes nucleic acid hybridization to detect the target nucleic acid, the kit may also have containers containing nucleotide(s) for amplification of the target nucleic acid sequence and/or a container comprising a reporter-means, such as a biotin-binding protein, such as avidin or streptavidin, bound to a reporter molecule, such as an enzymatic, florescent, or radionuclide label.

The following Examples are intended to illustrate, but not to limit the invention. While such Examples are typical of those that might be used, other procedures known to those skilled in the art may alternatively be utilized.

EXAMPLE 1

Identification and Purification of Nuclear Matrix Proteins

Patients

Fresh prostatic tissue was studied from 21 men undergoing radical retropubic prostatectomy for clinically localized (Stage B, T2) prostate cancer (N-19) (Gleason grade 5–9) or open prostatectomy for benign prostatic hyperplasia (BPH, N=2).

Tissue Preparation

Fresh tissue was obtained within 15 minutes of surgical removal. Approximately one gram of gross tumor was taken from a palpable tumor nodule from 14 specimens. One gram of normal prostate tissue was obtained from the prostatic lobe contralateral to the tumor nodule in 13 specimens. One gram of BPH tissue was obtained from the periurethral region of the contralateral lobe in 12 specimens and 25–30 grams from each of the 2 open prostatectomy specimens. All tissues removed were histologically confirmed with hematoxylin and eosin sections on both the proximal and distal ends of the section.

Purification of Nuclear Matrix Proteins

Nuclear matrix proteins were isolated according to the methodology of Fey and Penman (*Proc. Nail. Acad. Sci., USA,* 85:121–125, 1988). Briefly, fresh human prostate tissue was minced into small (1 mm$^3$) pieces and homogenized with a Teflon pestle on ice with 0.5% Triton X-100 in a solution containing 2 mM vanadyl ribonucleoside (RNAase inhibitor) containing 1 mM phenylmethylsulfonyl fluoride (serine protease inhibitor) to release the lipids and soluble proteins. Extracts were then filtered through a 350 micron nylon mesh and extracted with 0.25 M ammonium sulfate to release the soluble cytoskeletal elements. DNase treatment at 25° C. was used to remove the soluble chromatin. The remaining fraction contained intermediate filaments and nuclear matrix proteins. This fraction was then disassembled with 8 M urea, and the insoluble components, which consist principally of carbohydrates and extracellular matrix components, were pelleted. The urea was dialyzed out and the intermediate filaments allowed to reassemble and were removed by centrifugation. The nuclear matrix proteins were then ethanol precipitated. Protein concentrations were determined with the Comassie$^R$ Plus protein assay reagent kit (Pierce, Rockfcrd, Ill.) with bovine serum albumin as a standard. For preparation for gel electrophoresis, the nuclear matrix proteins were redissolved in a sample buffer consisting of 9 M urea, 65 mM 3-[( cholamidopropyl) dimethylamino)-1-propanosulfonate, 2.2% ampholytes and 140 mM dithiothreitol.

Two-Dimensional Electrophoresis

High resolution two-dimensional gel electrophoresis was carried out utilizing the Investigator 2-D gel system (Milligan/Biosearch, Bedford, Mass.) (Patton, W. F., et al., *BioTechniques,* 8:518–527, 1990. One-dimensional isoelectric focusing was carried out for 18,000 V-h using 1 nm×18 on tube gels after 1.5 hours of prefocusing. The tube gels were extruded and placed on top of 1-mm pre-cast 10% Tris-acetate sodium dodecyl sulfate Duracryl™ (Millipore, Colo., Bedford, Mass.) high tensile strength (HTS) polyacrylamide electrophoresis slab gels and the gels were electrophoresed with 12° C. constant temperature regulation for approximately 5 hours. Gels were fixed with 50% methanol and 10% acetic acid. After thorough rinsing and rehydration, gels were treated with 5% glutaraldehyde and 5 mM dithiothreitol after buffering with 50 Mm phosphate (pH 72). Gels were stained with silver stain using the methodology of Wray (Wray, W. et al., *Anal. Biochem,* 118:197–203, 1981) (Accurate Chemical Co., Inc., Westbury, N.Y.). Fifty micrograms of nuclear matrix protein were loaded for each gel. Protein molecular weight standards were determined with the GELCODE (Dacheng, H., et al., *J. Cell Biol.,* 110:569–580, 1990), protein molecular weight market kit (MW 12,400–97,400), (Pierce, Rockford, Ill.). Isoelectric points were determined using carbamylated creatine kinase standards (pH 7.0–4.950, (BDH Limited, England)). Only protein spots clearly and reproducibly observed or absent in all samples from the various tissues were considered when determining variations in nuclear matrix proteins between tissues.

There was marked similarity seen in the nuclear matrix protein patterns between patients with approximately 120 of 150 proteins spots consistently seen from patient to patient. Fourteen nuclear matrix proteins were identified that were consistently present or absent when comparing normal prostate BPH and prostate cancer. A protein (PC-1), with a molecular weight of 56 Kd and pl=6.58, represented a nuclear matrix protein that appeared in all (14/14) human prostate cancer specimens studied but was not detected in any normal prostate (0/13) or BPH tissue (0/14).

FIG. 1 shows nuclear matrix protein composition of normal human prostate (A), benign prostatic hyperplasia (B) and prostate cancer (C). Four proteins known to be present in most nuclear matrix preparations, lamin A, lamin B, lamin C and actin were identified based upon previously reported molecular weights and isoelectric points (Fey, E. G., et a., *Proc. Natl. Acad. Sci. USA,* 85:121–125, 1988) and labeled on FIG. 1A as LA, LB, LC and A respectively.

Figure 1B:
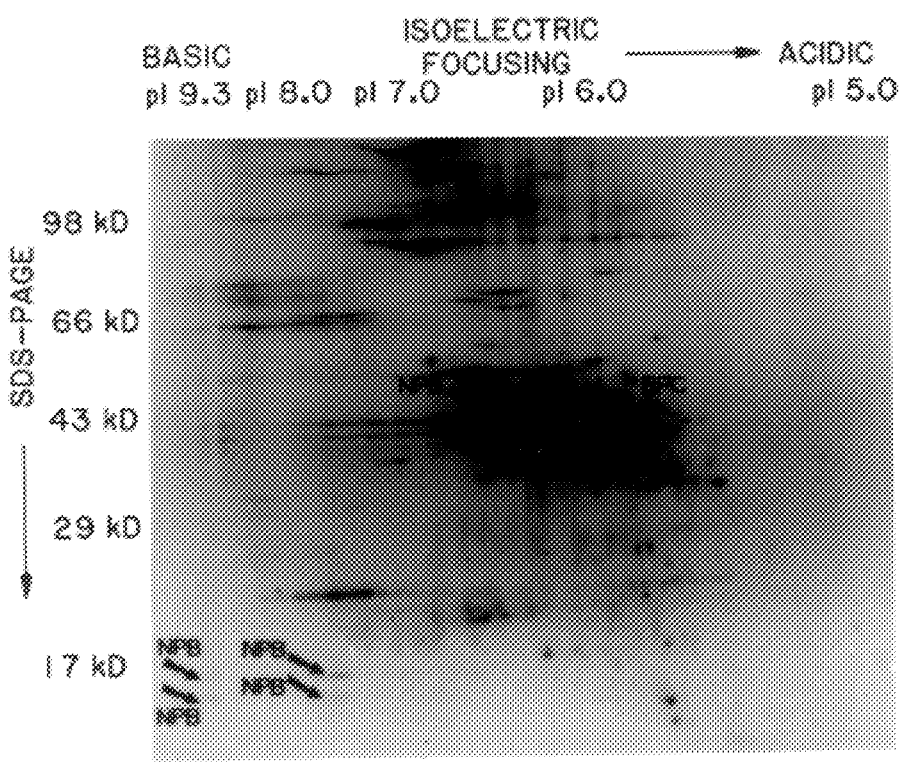
Figure 1C:
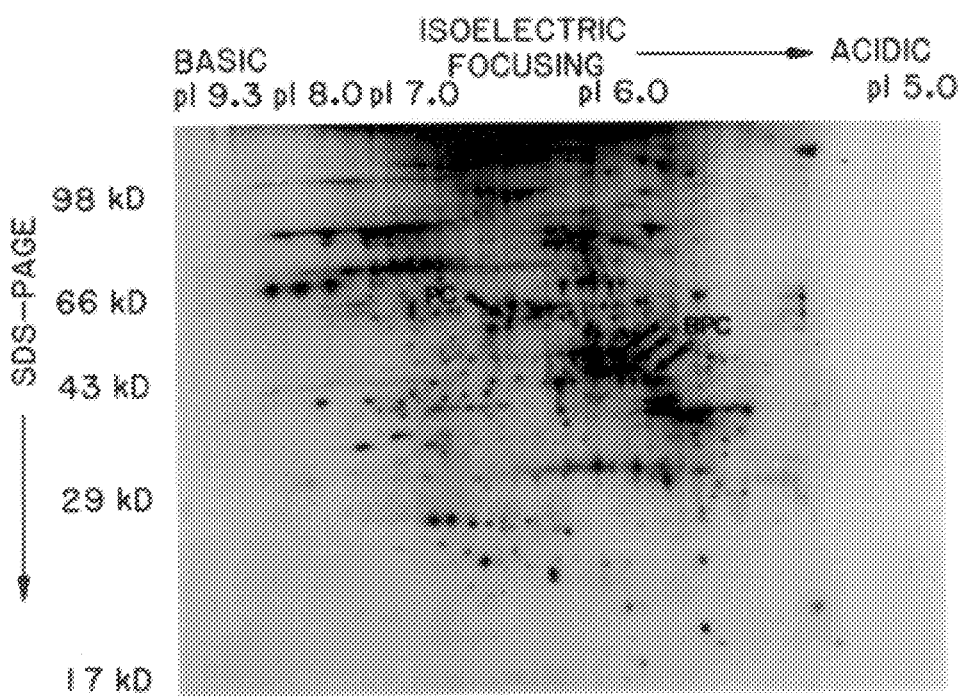

FIG. 1 demonstrates the typical high resolution two-dimensional gel electrophoresis patterns for nuclear matrix proteins isolated from normal human prostate (FIG. 1A), human BPH (FIG. 1B) and human prostate cancer (FIG. 1C). Gel spots differing between normal prostate, BPH and prostate cancer (in all specimens examined) have been marked with arrows and identified with labels corresponding to those in Table 1. Table 1 demonstrates the molecular weight and isoelectric points of the 14 different protein spots found to be consistently present or absent when comparing nuclear matrix proteins from normal prostate, BPH and prostate cancer tissue for this group of 21 patients.

Figure 2:
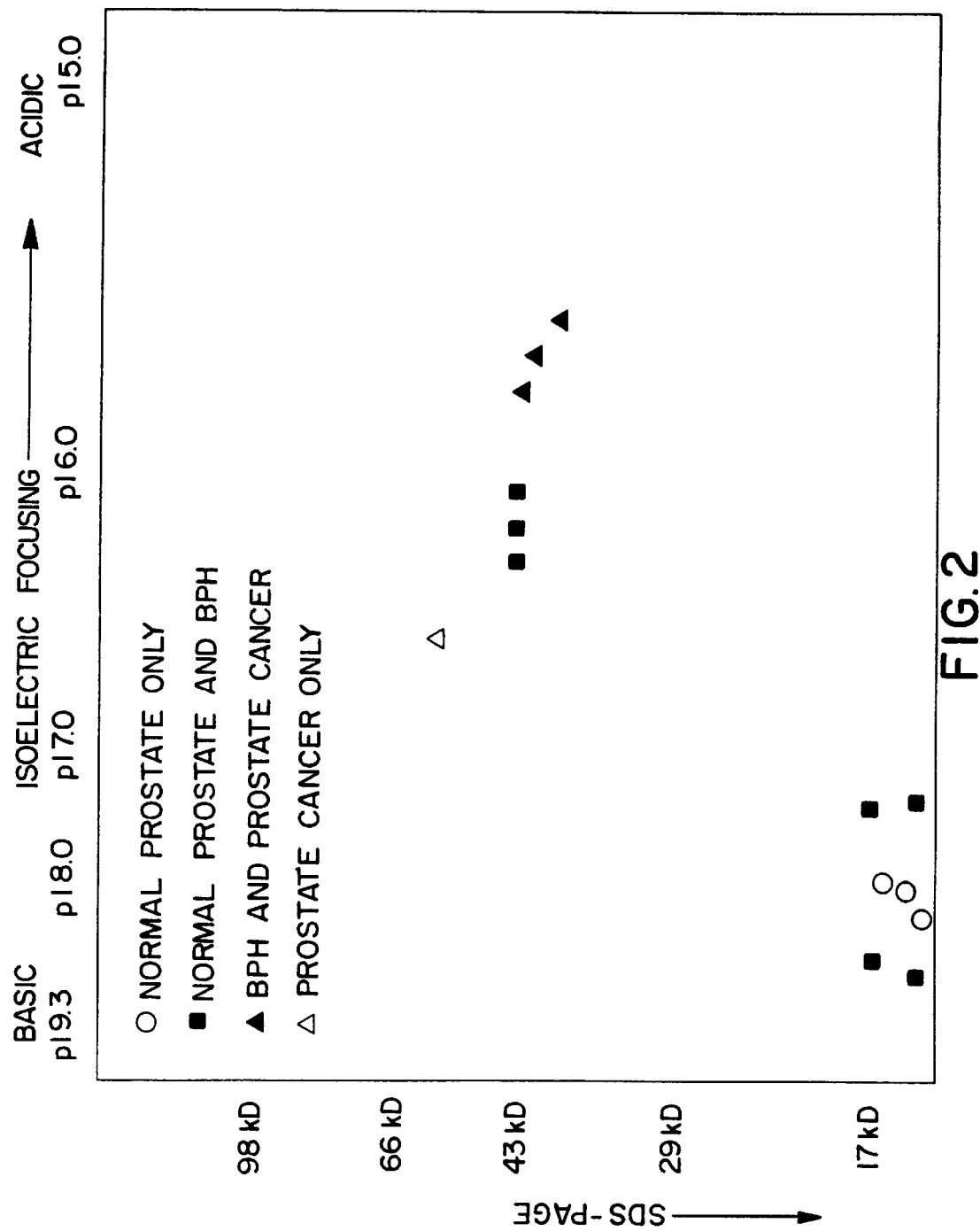
FIG. 2 shows specific nuclear matrix proteins in BPH and prostate cancer. Schematic of major tissue specific nuclear matrix proteins of normal prostate, BPH and prostate cancer. Abbreviations: kD—molecular weight in thousands, SDS-PAGE—sodium dodecyl sulfate-polyacrylamide gel electrophoresis and pI—isoelectric point and BPH—benign prostatic hyperplasia.

FIG. 2 summarizes the location of the protein spots that differed between the various tissues and shows specific nuclear matrix proteins in BPH and prostate cancer. Schematic of major tissue specific nuclear matrix proteins of normal prostate, BPH and prostate cancer. Abbreviations: kD—molecular weight in thousands, SDS-PAGE—sodium dodecyl sulfate-polyacrylamide gel electrophoresis and pl—isoelectric point and BPH—benign prostatic hyperplasia.

No NMPs were detected which were present only in BPH and were absent in normal prostate and prostate cancer. Likewise, no NMP's were present both in normal prostate and prostate cancer, but were absent in BPH. PC-1 (molecular weight 56 Kd and isoelectric point 6.58) represents an NMP seen only in human prostate cancer tissue and was consistently absent in all normal prostate and BPH samples. In additional testing, PC-1 was found in kidney and bladder cancer specimens, but was not detected in normal kidney or bladder tissue.

The absence of NPB-1-7 and NP-1-3 in malignant cells suggests that genes encoding these NMPs may function as cancer suppressor genes. This is especially true with respect to NP-1-3 which were also absent in benign hyperplastic tissue.

TABLE 1

NUCLEAR MATRIX PROTEINS FROM FRESH NORMAL PROSTATE. BPH AND PROSTATE CANCER TISSUE

| Protein | M$_r$ | pl | Normal (N = 13) | BPH (N = 14) | Cancer (N = 14) |
|---|---|---|---|---|---|
| NPB-1 | 17,000 | 6.91 | + | + | − |
| NPB-2 | 17,000 | 8.30 | + | + | − |
| NPB-3 | 12,000 | 8.40 | + | + | − |
| NPB-4 | 12,000 | 6.91 | + | + | − |
| NPB-5 | 43,000 | 6.27 | + | + | − |
| NPB-6 | 43,000 | 6.22 | + | + | − |
| NPB-7 | 43,000 | 6.14 | + | + | − |
| NP-1 | 12,000 | 7.50 | + | − | − |
| NP-2 | 11,500 | 7.62 | + | − | − |
| NP-3 | 11,000 | 8.30 | + | − | − |
| BPC-1 | 42,500 | 5.80 | − | + | + |
| BPC-2 | 42,000 | 5.73 | − | + | + |
| BPC-3 | 41,000 | 5.64 | − | + | + |
| PC-1 | 56,000 | 6.58 | − | − | + |

NP—Normal Prostate
BPH Benign Prostate Hyperplasia.
PC—Prostate Cancer; NPB—Both Normal and Benign Hyperplasia Prostate Tissue; BPC—Benign Hyperplasia and Cancerous Prostate Tissue.

The designation of each protein corresponds to the identified proteins in FIG. 1.

EXAMPLE 2

Models for Progression from Normal Prostate Cells to Prostatic Cancer

Although the precise molecular and/or environmental events necessary for the development of prostatic disease are largely unknown, it has been well established that the development of prostate cancer is a multistep process (Carter, H. B., et al., *J. Urol.*, 143:742–746, 1990). Epidemiologic studies based on the original work of Ashley (Ashley, D. F. B., *J. Path. Bact.*, 90:217–225, 1965) and Armitage and Doll (Armitage P. and Doll, R., *Brit J. Cancer*, 8:1–15, 1954) using age specific incidence rates for prostate cancer and BPH in the United States demonstrate that development of BPH is most likely a two-step process while the development of clinically evident prostate cancer most likely involves a multi-step (greater than 2 event) process (Carter, H. B., et al., *J. Urol.*, 143:742–746, 1990).

Figure 3:
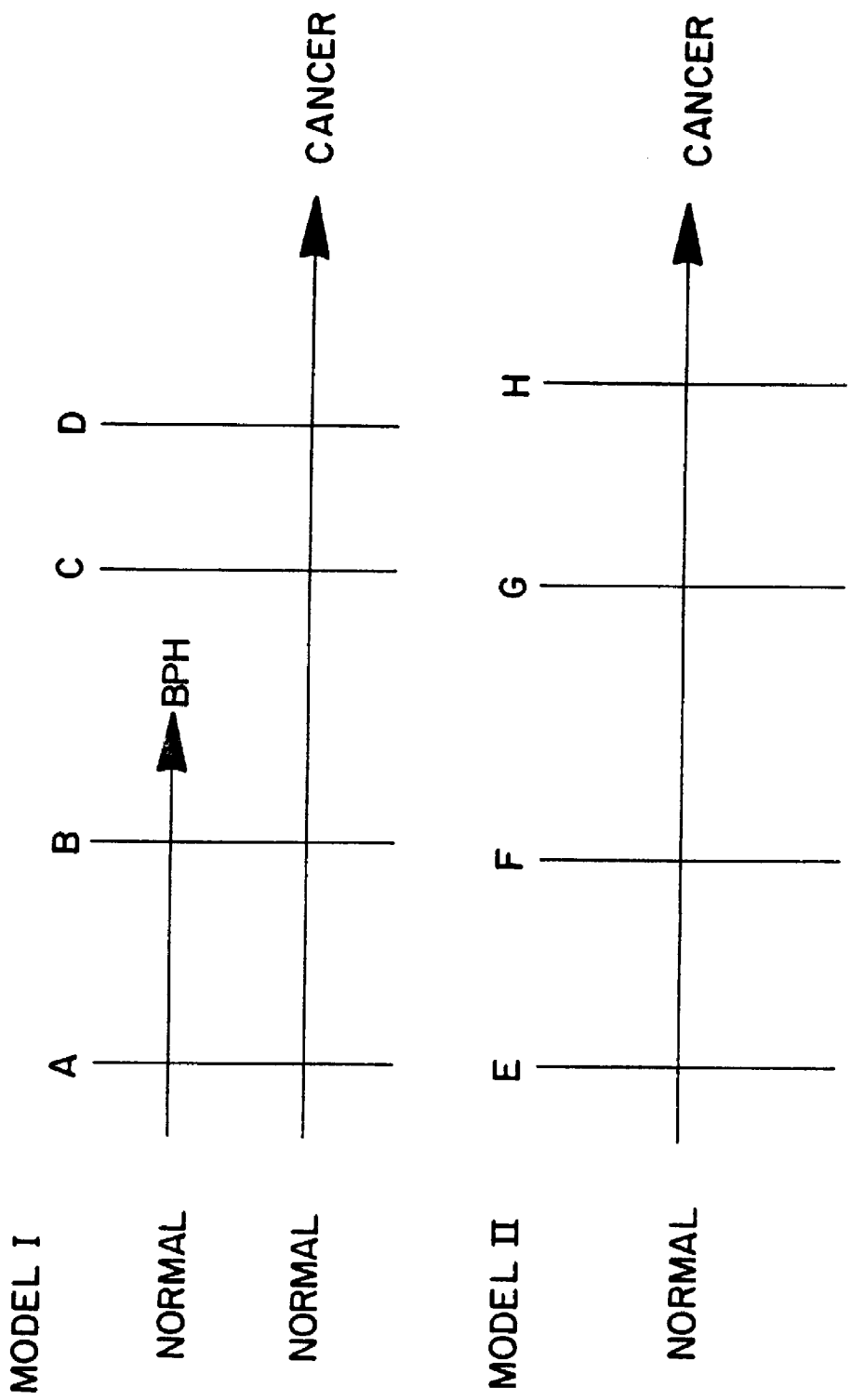
FIG. 3 shows two models of multistep progression from normal prostate (Normal) to benign prostatic hyperplasia (BPH) or to prostate cancer (Cancer). Model I predicts that similar events occur in both pathways. Model II predicts different events occurring when progressing from normal to BPH as when progressing to cancer.

Two different models can be postulated for the progression of a normal prostatic epithelial cell to either BPH or prostate cancer. FIG. 3 shows two models of multistep progression from normal prostate (Normal) to benign prostatic hyperplasia (BPH) or to prostate cancer (Cancer). Model I predicts that similar events occur in both pathways. Model II predicts different events occurring when progressing from normal to BPH as when progressing to cancer. The first model (Model I) predicts that the early events for progression from either normal to BPH or normal to prostate cancer are similar (events A–B in Model I). The second model (Model II) predicts that progression for BPH and cancer would undergo different events (events A–B versus events E–H). Using the presence or absence of nuclear matrix proteins as a phenotypic marker to test these models, it would be predicted that Model I would be satisfied if a specific group of protein spots were either absent or present in both BPH and prostate cancer (NP 1–3, BPC 1–3) and additional protein spots were present or absent in only prostate cancer (NPB 1–7 or PC-1). Thus all of the differences observed in the nuclear matrix proteins satisfied Model I. In order to satisfy Model II, a protein(s) need be present or absent in BPH only and this was not observed in any samples. Thus, these data support Model I in which similar phenotypic expressions are occurring in the nuclear matrix of cells progressing to BPH as those cells progressing to prostate cancer. As a result, the NMPs of the invention can be used to monitor and detect the stage and progression of a cell proliferative disorder, such as prostate cancer, from normalcy to benign disease to malignancy. This information, in turn, can be used to initiate appropriate therapy.

The foregoing is meant to illustrate, but not to limit, the scope of the invention. Indeed, those of ordinary skill in the art can readily envision and produce further embodiments, based on the teachings herein, without undue experimentation.

We claim:

1. An in vitro method for detecting a prostatic or urogenital cell proliferative disorder in a subject comprising contacting a specimen suspected of containing a protein selected from the group consisting of Normal and Benign Hyperplasia Prostate Tissue-1 (NPB-1), Normal and Benign Hyperplasia Prostate Tissue-2 (NPB-2), Normal and Benign Hyperplasia Prostate Tissue-3 (NPB-3), Normal and Benign Hyperplasia Prostate Tissue-4 (NPB-4), Normal and Benign Hyperplasia Prostate Tissue-5 (NPB-5), Normal and Benign Hyperplasia Prostate Tissue-6 (NPB-6), Normal and Benign Hyperplasia Prostate Tissue-7 (NPB-7), Benign Hyperplasia and Cancerous Prostate Tissue-1 (BPC-1), Benign Hyperplasia and Cancerous Prostate Tissue-2 (BPC-2), Benign Hyperplasia and Cancerous Prostate Tissue-3 (BPC-3), and Prostate Cancer-1 with a reagent which binds to at least one of the protein and detecting binding of the reagent to at least one of the proteins in the specimen, wherein the presence of at least one of the proteins is indicative of a prostatic or urogenital cell proliferative disorder.

2. The method of claim 1, wherein the reagent is an antibody.

3. The method of claim 2, wherein the antibody is polyclonal.

4. The method of claim 2, wherein the antibody is monoclonal.

* * * * *